(12) United States Patent
De Reuse et al.

(10) Patent No.: US 6,416,968 B1
(45) Date of Patent: Jul. 9, 2002

(54) **METHODS OF INHIBITING *HELICOBACTER PYLORI***

(75) Inventors: Hilde De Reuse; Stéphane Skouloubris; Valérie Cussac, all of Paris; Agnès Labigne, Burress/Yvette, all of (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/643,914

(22) Filed: Aug. 23, 2000

Related U.S. Application Data (63) Continuation of application No. 09/107,383, filed on Jun. 30, 1998, now Pat. No. 6,190,667.

(51) Int. Cl.$^7$ .................................................. C12Q 1/18
(52) U.S. Cl. ........................... 435/32; 435/69.1; 435/6; 435/18; 435/12; 435/29; 435/4; 435/106; 435/252.1; 530/350; 530/300; 514/230.5; 514/44; 424/94.1; 424/141.1; 424/150.1; 424/234.1; 424/184.1; 424/236.1
(58) Field of Search .................. 514/230.5, 44, 514/29; 530/350, 300; 435/6, 375, 184, 69.2, 69.1, 18, 106, 252.3, 12, 29, 4; 424/184.1, 236.1, 141.1, 234.1, 150.1, 94.1

(56) References Cited

U.S. PATENT DOCUMENTS

| | | | |
|---|---|---|---|
| 5,472,695 A | 12/1995 | Neeman et al. | |
| 5,560,912 A | 10/1996 | Neeman et al. | |
| 5,695,931 A | 12/1997 | Labigne et al. | |
| 5,843,460 A | 12/1998 | Labigne et al. | |
| 5,876,946 A | 3/1999 | Burbaum et al. | |
| 5,942,409 A | 8/1999 | Sachs et al. | |
| 5,985,631 A | * 11/1999 | Soman et al. ............... | 435/184 |
| 5,986,051 A | * 11/1999 | Labigne et al. ............. | 530/350 |
| 6,027,878 A | * 2/2000 | Labigne et al. ............. | 435/6 |
| 6,087,358 A | * 7/2000 | Baker et al. ............... | 514/230.5 |
| 6,124,271 A | * 9/2000 | Iversen et al. .............. | 514/44 |

FOREIGN PATENT DOCUMENTS

| | | |
|---|---|---|
| EP | A 0367 644 | 5/1990 |
| EP | 0 745 674 | 5/1996 |
| WO | WO 91 09049 | 6/1991 |
| WO | 93/07273 | 4/1993 |
| WO | 94/09823 | 5/1994 |
| WO | 94/26901 | 11/1994 |
| WO | WO 96 33732 | 10/1996 |
| WO | 96/40893 | 12/1996 |
| WO | WO 96 40893 | 12/1996 |

OTHER PUBLICATIONS

Nagata, K et al, Antimicrobial Agents and Chemotherapy, vol. 39, pp. 567–570, 1995.*

Mirshahi, F et al, Journal of Clinical Pathology, Mar. 1998, vol. 51(3), pp. 220–224.*

Kuhler et al, J. Med. Chem., vol. 38, pp. 4906–4916, 1995.*

Coudron, PE et al, Journal of Clinical Microbiology, vol. 33(4), pp. 1028–1030, Apr. 1995.*

Garcia–Rodriguez, JA et al, Revista Espanola de Quimioterapia, Spain, vol. 4(4), pp. 336–337, 1991.*

DeCross, AJ et al, Journal of Clinical Microbiology, vol. 31(8), pp. 1971–1974, Aug. 1993.*

(List continued on next page.)

*Primary Examiner*—Lynette R. F. Smith
*Assistant Examiner*—Ginny Allen Portner
(74) *Attorney, Agent, or Firm*—Finnegan, Henderson, Farabow, Garrett & Dunner (57) ABSTRACT

This invention relates to methods of screening molecules capable of inhibiting the survival of *Helicobacter pylori* in vivo by specifically inhibiting the activity of UreI, to the molecules identified by these methods, and to the use of these molecules to treat or prevent *H. pylori* infection.

9 Claims, 4 Drawing Sheets

OTHER PUBLICATIONS

Coudron, PE et al, Antimicrobial agents and chemotherapy, vol. 39(1), pp. 66–69, Jan. 1995.*

Coudron, PE et al, Antimicrobial agents and chemotherapy, vol. 39(12), pp. 2641–2644, Dec. 1995.*

McGowan, CC et al, Gastroenterology, vol. 107(3), pp. 738–743, Sep. 1994.*

Park, J et al, Biol. Pharm. Bull, vol. 19(2), pp. 182–187, Feb. 1996.*

Sjostrom, JE et al, J. Med. Microbiology, vol. 44,(6), pp. 425–433, Jun. 1996.*

Midolo, PD et al, Journal of Gastroenterology and Hepatology, vol. 11(3), pp. 290–292, Mar. 1996.*

Ito, Y et al, European Journal of pharmacology, Mar. 19, 1998, vol. 345(2), pp. 193–198.*

Pope, AJ et al, Digestive diseases and sciences, vol. 43(1), pp. 109–119, Jan. 1998.*

V. Cussac et al., "Expression of Helicobactor pylori Urease Activity in Escherichia coli Host Strains," Society for Microbial Ecology and Disease, vol. 4(S), Oct. 1991, p. S139, Abstract H4–4.

Sugiyama, et al., "A Novel Enzyme Immunoassay for Serodiagnosis of *Helicobacter pylori* Infection," Gastroenterology, 101:77–83 (1991).

V. Cussac et al., Expression of Helicobacter pylori Urease Genes in Escherichia coli Grown under Nitrogen–Limiting Conditions, Journal of Bacteriology 174(8):2466–2473 (Apr. 1992).

R. Ferrero et al., "Construction of Urease Deficient Mutants of Helicobacter pylori By Allelic Exchange," Society for Microbial Ecology and Disease, vol. 4(S), Oct. 1991, p. S139, Abstract H4–4.

A. Labigne et al., Bull. Acad. Natle. Med. 175(6):791–802 (1991).

Labigne et al., J. Bacteriol., Mar. 1991, vol. 173(6), pp. 1920–1931.

Cussac et al., J. Bacteriol., vol. 174(8), pp. 2466–2473.

Eaton et al., Infection Immunity, Jul. 1991, vol. 59(7), pp. 2470–2475.

Akada et al., Gut, vol. 41 (suppl. 1), pp. A7–A–8, Sep. 11–14, 1997.

S. Skouloubris, J–M Thiberge, A. Labigne, H. DeReuse: "The Helicobacter Pylori UreI Protein Is Not Involved in Urease Activity But Is Essential For Bacterial Survival In Vivo" Infection and Immunity, vol. 66, No. 9, Sep. 1988, pp. 4517–4521.

M. Clyne, A. Labigne, B. Drumm: Helicobacter Pylori Requires An Acidic Environment To Survive In The Presence of Urea: Infection and Immunity, vol. 63, No. 5, May 1995, pp. 1669–1673.

D. R. Scott, D. Weeks, C. Hong, S. Postius, K. Melchers, G. Sachs: "The Role of Internal Urease In Acid Resistance of Helicobacter Pylon" Gastroenterology, vol. 114, Jan. 1998, pp. 58–70.

* cited by examiner

```
UreI-Hp      1  MIGVLLYVGHVLLISNGLCGHTKVDPKSTAVMNFVGGLSIICNVMVI              48
UreI-Hf      1  MIGLVLLYAVMVLISNGLVSGLANVDAKSKAIMNYVGGDSPLCVMWSLS              49
UreI-Lacto   1                                                              0
UreI-Strepto 1  .......MCGVGFIVLAVLFIDGLMLIGRISPRGATPINFVGGIVVTPI....VLI        8
AmiS-Myco    1  MGSYGLLYVSAVMFVNGLMLIGTVPVRSASVILEVGAIOVVPT..VML              48
AmiS-Rhod    1  MGSVGLLYVSAVMFVNGLMLIGTVPVRSASVILEVGAIOVVPT..VML              48
AmiS-Pseudo  1  MIGVLMVVCGAVLFINAVWILGKISGREVAVINTVGVISACVAF..YLI              48

UreI-Hp     49  TYSALNPTAPVEGAEDIAQVSHHLTNFYGPAIGHLFGFTMLYAAINTF               97
UreI-Hf     50  SYSTFHPTPPATGPEDVAQVSQHLINFYGPAIGLLFGFTYLYAAINTF               98
UreI-Lacto   1                                                              0
UreI-Strepto 9  YGACTGQGA..........EWIVGSATGILFAFTYLYSAINTIF                  42
AmiS-Myco   49  LQSGGDAAV..........FAASGIYLFGFTYIMVAAINNVT                    80
AmiS-Rhod   49  IQAQGDSSA..........VLAASGIYIFGFTYLYNGLSNLA                    80
AmiS-Pseudo 49  FSAAAGQGS..........KAGATLLFAFTYIMVAAANQFL                     80

UreI-Hp     98  GLDWRPYSMSLFVAINTIPAAILSHYSDMLDDHKVLGITEGDWAIIW              146
UreI-Hf     99  NLDWKPYCWVCLFVINTIPAAILSHYSDALDDHRLLGITEGDWAFLW              147
UreI-Lacto   1                                                              0
UreI-Strepto 43 DFDQRLYGWFSLFVAINTLPAGHICLTS..........GYGGNAWYGHFW            82
AmiS-Myco   81  DWDGEGIGWFSLFVAIAALGVSWHAFTAEADPA.....FGVIW                  118
AmiS-Rhod   81  GFEPEGIGWFSLFVACAALVSFLSFTVSNDPV.....FGVIW                   118
AmiS-Pseudo 81  EVDGKGLGWFLFVSLTACIVAFAGASGPF.........GLWNAVNW               121
```

FIG. 3

| | | | | |
|---|---|---|---|---|
| UreI-Hp | 147 | ...IAWGVLWLTAEIENILKIPLGKFLPWFAILEGILTAWIIPAWLFIQHW | 194 | SEQ ID NO: 10 |
| UreI-Hf | 148 | ...IAWGVTWMLIGWIECALGK-SLGKFVPWFAIVEGVITAWIIPAWLFIQHW | 195 | SEQ ID NO: 11 |
| UreI-Lacto | 1 | ...MMIHGFTHNNL-KMNLGKFPCY-IIEGTCTAWMLPAMLLNYW | 44 | SEQ ID NO: 12 |
| UreI-Strepto | 83 | ...ELWGILWLIIAFIEFITLGLNLKK-NLGKFVPYFAIIEGYIFTAWECIVMLGK | 130 | SEQ ID NO: 13 |
| AmiS-Myco | 119 | ...LMAVLMFMIFILGHDALGFAAVGFVWAVPAFLYAVPAELLVSGNW | 167 | SEQ ID NO: 14 |
| AmiS-Rhod | 119 | ...MTLFFIVMIGLGRENLSRFTIGLWAAILSQPTLYPAFIIIGNF | 167 | SEQ ID NO: 15 |
| AmiS-Pseudo | 122 | ...TVWAIMFCFFILGLSR-GIQKPVAYLLASALLTAWEIGLLILGQVL | 169 | SEQ ID NO: 16 |

| | | | | |
|---|---|---|---|---|
| UreI-Hp | 195 | V | 196 | SEQ ID NO: 10 |
| UreI-Hf | 196 | S | 196 | SEQ ID NO: 11 |
| UreI-Lacto | 45 | PN | 47 | SEQ ID NO: 12 |
| UreI-Strepto | 131 | | 131 | SEQ ID NO: 13 |
| AmiS-Myco | 168 | ETGPLPAAVIAVTGFAAVVLAYPTGPRLAAPSVTNPPPAALAATTR | 213 | SEQ ID NO: 14 |
| AmiS-Rhod | 168 | HTTPAVAAGMA----GALLVLLGLAKTLAAPKAAVPQRPVFN | 206 | SEQ ID NO: 15 |
| AmiS-Pseudo | 170 | KA | 173 | SEQ ID NO: 16 |

*FIG. 3 CONT.*

SEQUENCE LISTING

```
<160> NUMBER OF SEQ ID NOS: 16

<210> SEQ ID NO 1
<211> LENGTH: 25
<212> TYPE: DNA
<213> ORGANISM: primer

<400> SEQUENCE: 1
tttgacttac tggggatcaa gcctg                                  25

<210> SEQ ID NO 2
<211> LENGTH: 34
<212> TYPE: DNA
<213> ORGANISM: adaptor

<400> SEQUENCE: 2
gatcatttat tcctccagat ctggaggaat aaat                        34

<210> SEQ ID NO 3
<211> LENGTH: 29
<212> TYPE: DNA
```

-continued

<213> ORGANISM: primer

<400> SEQUENCE: 3
gaagatctct aggacttgta ttgttatat                               29

<210> SEQ ID NO 4
<211> LENGTH: 23
<212> TYPE: DNA
<213> ORGANISM: primer

<400> SEQUENCE: 4
tatcaacggt ggtatatcca gtg                                     23

<210> SEQ ID NO 5
<211> LENGTH: 23
<212> TYPE: DNA
<213> ORGANISM: primer

<400> SEQUENCE: 5
gcagttattg gtgcccttaa acg                                     23

<210> SEQ ID NO 6
<211> LENGTH: 23
<212> TYPE: DNA
<213> ORGANISM: primer

<400> SEQUENCE: 6
ccggtgatat tctcatttta gcc                                     23

<210> SEQ ID NO 7
<211> LENGTH: 20
<212> TYPE: DNA
<213> ORGANISM: primer

<400> SEQUENCE: 7
gcgagtatgt aggttcagta                                         20

<210> SEQ ID NO 8
<211> LENGTH: 25
<212> TYPE: DNA
<213> ORGANISM: primer

<400> SEQUENCE: 8
gtgatacttg agcaatatct tcagc                                   25

<210> SEQ ID NO 9
<211> LENGTH: 27
<212> TYPE: DNA
<213> ORGANISM: primer

<400> SEQUENCE: 9
caaatccaca taatccacgc tgaaatc                                 27

<210> SEQ ID NO 10
<211> LENGTH: 195
<212> TYPE: PRT
<213> ORGANISM: H. pylori

<400> SEQUENCE: 10

Met Leu Gly Leu Val Leu Leu Tyr Val Gly Ile Val Leu Ile Ser Asn
 1               5                  10                  15

Gly Ile Cys Gly Leu Thr Lys Val Asp Pro Lys Ser Thr Ala Val Met
            20                  25                  30

```
Asn Phe Phe Val Gly Gly Leu Ser Ile Ile Cys Asn Val Val Ile
         35                  40                  45

Thr Tyr Ser Ala Leu Asn Pro Thr Ala Pro Val Glu Gly Ala Glu Asp
 50                  55                  60

Ile Ala Gln Val Ser His His Leu Thr Asn Phe Tyr Gly Pro Ala Thr
 65                  70                  75                  80

Gly Leu Leu Phe Gly Phe Thr Tyr Leu Tyr Ala Ala Ile Asn His Thr
                 85                  90                  95

Phe Gly Leu Asp Trp Arg Pro Tyr Ser Trp Tyr Ser Leu Phe Val Ala
                100                 105                 110

Ile Asn Thr Ile Pro Ala Ala Ile Leu Ser His Tyr Ser Asp Met Leu
            115                 120                 125

Asp Asp His Lys Val Leu Gly Ile Thr Glu Gly Asp Trp Ala Ile
130                 135                 140

Ile Trp Leu Ala Trp Gly Val Leu Trp Leu Thr Ala Phe Ile Glu Asn
145                 150                 155                 160

Ile Leu Lys Ile Pro Leu Gly Lys Phe Thr Pro Trp Leu Ala Ile Ile
                165                 170                 175

Glu Gly Ile Leu Thr Ala Trp Ile Pro Ala Trp Leu Leu Phe Ile Gln
                180                 185                 190

His Trp Val
        195

<210> SEQ ID NO 11
<211> LENGTH: 196
<212> TYPE: PRT
<213> ORGANISM: H. felis

<400> SEQUENCE: 11

Met Leu Gly Leu Val Leu Leu Tyr Val Ala Val Leu Ile Ser Asn
  1               5                  10                  15

Gly Val Ser Gly Leu Ala Asn Val Asp Ala Lys Ser Lys Ala Ile Met
             20                  25                  30

Asn Tyr Phe Val Gly Gly Asp Ser Pro Leu Cys Val Met Trp Ser Leu
         35                  40                  45

Ser Ser Tyr Ser Thr Phe His Pro Thr Pro Ala Thr Gly Pro Glu
 50                  55                  60

Asp Val Ala Gln Val Ser Gln His Leu Ile Asn Phe Tyr Gly Pro Ala
 65                  70                  75                  80

Thr Gly Leu Leu Phe Gly Phe Thr Tyr Leu Tyr Ala Ala Ile Asn Asn
                 85                  90                  95

Thr Phe Asn Leu Asp Trp Lys Pro Tyr Gly Trp Tyr Cys Leu Phe Val
                100                 105                 110

Thr Ile Asn Thr Ile Pro Ala Ala Ile Leu Ser His Tyr Ser Asp Ala
            115                 120                 125

Leu Asp Asp His Arg Leu Leu Gly Ile Thr Glu Gly Asp Trp Trp Ala
130                 135                 140

Phe Ile Trp Leu Ala Trp Gly Val Leu Trp Leu Thr Gly Trp Ile Glu
145                 150                 155                 160

Cys Ala Leu Gly Lys Ser Leu Gly Lys Phe Val Pro Trp Leu Ala Ile
                165                 170                 175

Val Glu Gly Val Ile Thr Ala Trp Ile Pro Ala Trp Leu Leu Phe Ile
                180                 185                 190

Gln His Trp Ser
```

195

<210> SEQ ID NO 12
<211> LENGTH: 46
<212> TYPE: PRT
<213> ORGANISM: Lactobacillus fermentum

<400> SEQUENCE: 12

Ile Leu Trp Leu Thr Gly Phe Leu Thr Asn Asn Leu Lys Met Asn Leu
 1               5                  10                  15

Gly Lys Phe Pro Gly Tyr Leu Gly Ile Ile Glu Gly Ile Cys Thr Ala
            20                  25                  30

Trp Ile Pro Gly Phe Leu Met Leu Leu Asn Tyr Trp Pro Asn
        35                  40                  45

<210> SEQ ID NO 13
<211> LENGTH: 129
<212> TYPE: PRT
<213> ORGANISM: Streptococcus salivarius

<400> SEQUENCE: 13

Ile Leu Asn Ile Ile Val Ile Ala Tyr Gly Ala Cys Thr Gly Gln Gly
 1               5                  10                  15

Ala Glu Trp Phe Tyr Gly Ser Ala Thr Gly Leu Leu Phe Ala Phe Thr
            20                  25                  30

Tyr Leu Tyr Ser Ala Ile Asn Thr Ile Phe Asp Phe Asp Gln Arg Leu
        35                  40                  45

Tyr Gly Trp Phe Ser Leu Phe Val Ala Ile Asn Thr Leu Pro Ala Gly
    50                  55                  60

Ile Leu Cys Leu Thr Ser Gly Tyr Gly Gly Asn Ala Trp Tyr Gly Ile
65                  70                  75                  80

Ile Trp Phe Leu Trp Gly Ile Leu Trp Leu Thr Ala Phe Ile Glu Ile
                85                  90                  95

Asn Leu Lys Lys Asn Leu Gly Lys Phe Val Pro Tyr Leu Ala Ile Phe
            100                 105                 110

Glu Gly Ile Val Thr Ala Trp Ile Pro Gly Leu Leu Met Leu Trp Gly
        115                 120                 125

Lys

<210> SEQ ID NO 14
<211> LENGTH: 213
<212> TYPE: PRT
<213> ORGANISM: Myco. smegmatis

<400> SEQUENCE: 14

Met Gly Gly Val Gly Leu Phe Tyr Val Gly Ala Val Leu Ile Ile Asp
 1               5                  10                  15

Gly Leu Met Leu Leu Gly Arg Ile Ser Pro Arg Gly Ala Thr Pro Leu
            20                  25                  30

Asn Phe Phe Val Gly Gly Leu Gln Val Thr Pro Thr Val Leu Ile
        35                  40                  45

Leu Gln Ser Gly Gly Asp Ala Ala Val Ile Phe Ala Ala Ser Gly Leu
    50                  55                  60

Tyr Leu Phe Gly Phe Thr Tyr Leu Trp Val Ala Ile Asn Asn Val Thr
65                  70                  75                  80

Asp Trp Asp Gly Glu Gly Leu Gly Trp Phe Ser Leu Phe Val Ala Ile
                85                  90                  95

```
Ala Ala Leu Gly Tyr Ser Trp His Ala Phe Thr Ala Glu Ala Asp Pro
            100                 105                 110

Ala Phe Gly Val Ile Trp Leu Leu Trp Ala Val Leu Trp Phe Met Leu
        115                 120                 125

Phe Leu Leu Leu Gly Leu Gly His Asp Ala Leu Gly Pro Ala Val Gly
    130                 135                 140

Phe Val Ala Val Ala Glu Gly Val Ile Thr Ala Ala Val Pro Ala Phe
145                 150                 155                 160

Leu Ile Val Ser Gly Asn Trp Glu Thr Gly Pro Leu Pro Ala Ala Val
                165                 170                 175

Ile Ala Val Ile Gly Phe Ala Ala Val Val Leu Ala Tyr Pro Ile Gly
                180                 185                 190

Arg Arg Leu Ala Ala Pro Ser Val Thr Asn Pro Pro Ala Ala Leu
                195                 200                 205

Ala Ala Thr Thr Arg
    210

<210> SEQ ID NO 15
<211> LENGTH: 206
<212> TYPE: PRT
<213> ORGANISM: Rhodococcus sp.

<400> SEQUENCE: 15

Met Gly Ser Val Gly Leu Leu Tyr Val Gly Ala Val Leu Phe Val Asn
1               5                   10                  15

Gly Leu Met Leu Leu Gly Thr Val Pro Val Arg Ser Ala Ser Val Leu
                20                  25                  30

Asn Leu Phe Val Gly Ala Leu Gln Cys Val Val Pro Thr Val Met Leu
            35                  40                  45

Ile Gln Ala Gln Gly Asp Ser Ser Ala Val Leu Ala Ala Ser Gly Leu
        50                  55                  60

Tyr Leu Phe Gly Phe Thr Tyr Leu Tyr Val Gly Ile Ser Asn Leu Ala
65                  70                  75                  80

Gly Phe Glu Pro Glu Gly Ile Gly Trp Phe Ser Leu Phe Val Ala Cys
                85                  90                  95

Ala Ala Leu Val Tyr Ser Phe Leu Ser Phe Thr Val Ser Asn Asp Pro
            100                 105                 110

Val Phe Gly Val Ile Trp Leu Ala Trp Ala Ala Leu Trp Thr Leu Phe
        115                 120                 125

Phe Leu Val Leu Gly Leu Gly Arg Glu Asn Leu Ser Arg Phe Thr Gly
    130                 135                 140

Trp Ala Ala Ile Leu Leu Ser Gln Pro Thr Cys Thr Val Pro Ala Phe
145                 150                 155                 160

Leu Ile Leu Thr Gly Asn Phe His Thr Thr Pro Ala Val Ala Ala Gly
                165                 170                 175

Trp Ala Gly Ala Leu Leu Val Leu Leu Gly Leu Ala Lys Ile Leu Ala
                180                 185                 190

Ala Pro Lys Ala Ala Val Pro Gln Pro Arg Pro Val Phe Asn
                195                 200                 205

<210> SEQ ID NO 16
<211> LENGTH: 171
<212> TYPE: PRT
<213> ORGANISM: P. aeruginosa

<400> SEQUENCE: 16
```

-continued

```
Met Leu Gly Leu Val Leu Leu Tyr Val Gly Ala Val Leu Phe Leu Asn
 1           5                   10                  15

Ala Val Trp Leu Leu Gly Lys Ile Ser Gly Arg Glu Val Ala Val Ile
             20              25              30

Asn Phe Leu Val Gly Val Leu Ser Ala Cys Val Ala Phe Tyr Leu Ile
         35              40              45

Phe Ser Ala Ala Ala Gly Gln Gly Ser Leu Lys Ala Gly Ala Leu Thr
     50              55              60

Leu Leu Phe Ala Phe Thr Tyr Leu Trp Val Ala Ala Asn Gln Phe Leu
 65              70              75                      80

Glu Val Asp Gly Lys Gly Leu Gly Trp Phe Cys Leu Phe Val Ser Leu
             85              90              95

Thr Ala Cys Thr Val Ala Ile Glu Ser Phe Ala Gly Ala Ser Gly Pro
            100             105             110

Phe Gly Leu Trp Asn Ala Val Asn Trp Thr Val Trp Ala Leu Leu Trp
            115             120             125

Phe Cys Phe Phe Leu Leu Leu Gly Leu Ser Arg Gly Ile Gln Lys Pro
        130             135             140

Val Ala Tyr Leu Thr Leu Ala Ser Ala Ile Phe Thr Ala Trp Leu Pro
145             150             155             160

Gly Leu Leu Leu Leu Gly Gln Val Leu Lys Ala
                165             170
```

METHODS OF INHIBITING *HELICOBACTER PYLORI*

This is a continuation of application Ser. No. 09/107,383, filed Jun. 30, 1998, now U.S. Pat. No. 6,190,667 which is incorporated herein by reference.

This invention relates to methods of screening molecules capable of inhibiting the survival of Helicobacter, particularly *Helicobacter pylori*, in vivo by specifically inhibiting the activity of UreI, to the molecules identified by these methods, and to the use of these molecules to treat or prevent Helicobacter infection.

BACKGROUND OF INVENTION

*Helicobacter pylori* is a microaerophilic Gram-negative bacterium, which colonizes the gastric mucosa of humans (10). *H. pylori* is associated with gastritis and peptic ulcer disease and has been shown to increase the risk of gastric cancers. Urease is a major virulence factor of *H. pylori*. It is involved in neutralizing the acidic microenvironment of the bacterium and also plays a role in *H. pylori* metabolism (11, 26).

Figure 1:
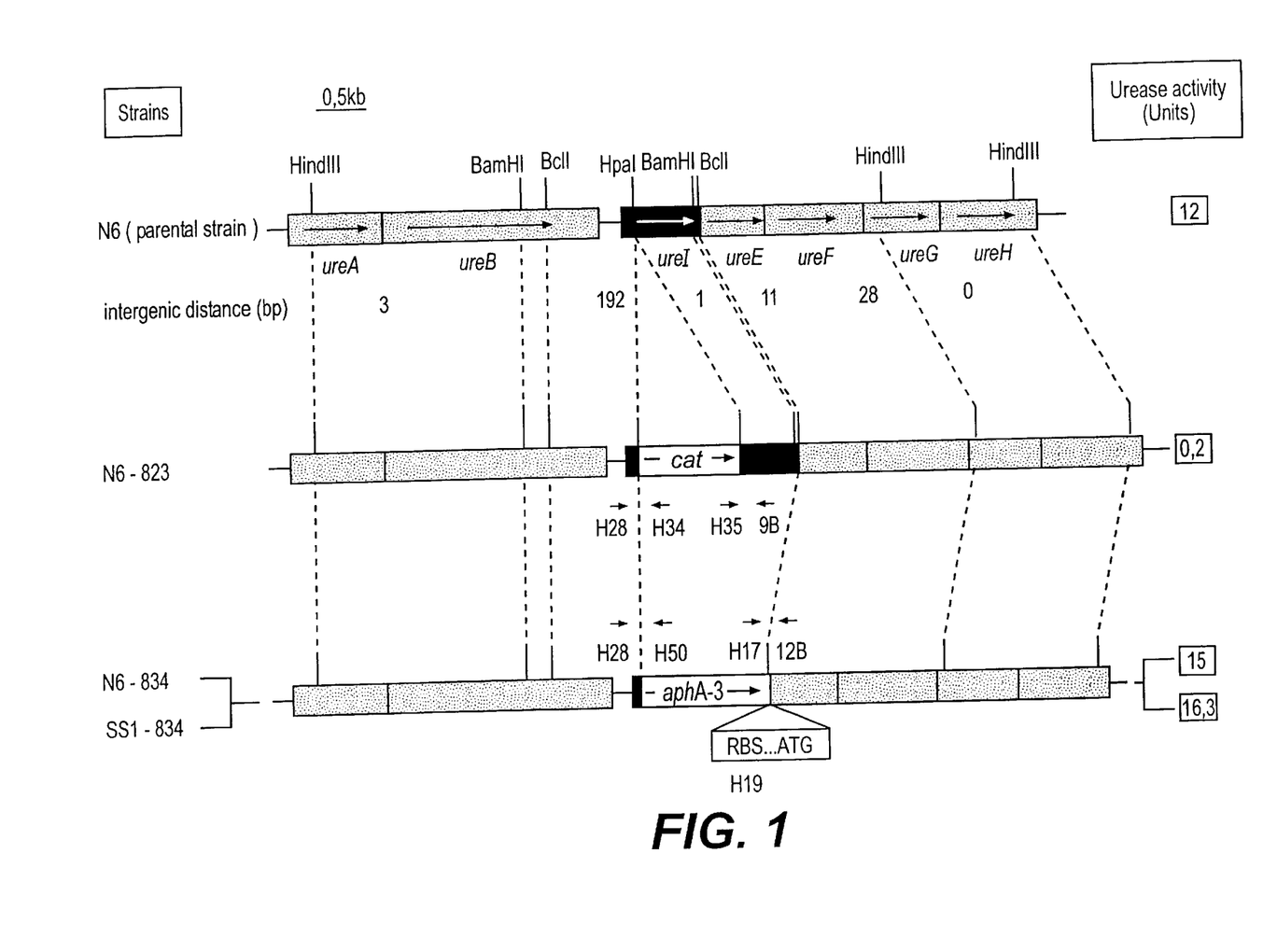

The urease region of the *H. pylori* genome is composed of two gene clusters common to all strains (9 and FIG. 1), one comprising the ureAB genes encoding the structural urease subunits and the other containing the ureEFGH genes encoding the accessory proteins required for nickel incorporation into the urease active site. The ureI gene lies immediately upstream from this latter gene cluster and is transcribed in the same direction (FIG. 1). The ureA, ureB, ureE, ureF, ureG, ureH, and ureI genes and gene products have been described and claimed in U.S. Pat. No. 5,695,931 and allowed patent application Ser. No. 08/472,285, both of which are specifically incorporated herein by reference.

The distances separating ureI from ureE (one base pair, bp) and ureE from ureF (11 bp) suggest that ureI-ureE-ureF constitute an operon. Cotranscription of ureI and ureE has been demonstrated by northern blot analysis (1). An *H. pylori* N6 mutant with a ureI gene disrupted by a MiniTn3-Km transposon was previously described by Ferrero et al. (1994) (13). This strain (N6-ureI::TnKm-8) presented a urease negative phenotype, so it was concluded that ureI was an accessory gene required for full urease activity.

The sequences of UreI from *H. pylori* and the AmiS proteins, encoded by the aliphatic amidase operons of *Pseudomonas aerziginosa* and Rhodococcus sp. R312, are similar (5, 27). Aliphatic amidases catalyze the intracellular hydrolysis of short-chain aliphatic amides to produce the corresponding organic acid and ammonia. It has been shown that *H. pylori* also has such an aliphatic amidase, which hydrolyzes acetamide and propionamide in vitro (23).

In view of the sequence similarity between UreI and AmiS together with the very similar structures of the urease and amidase substrates (urea: $NH_2$—CO—$NH_2$ and acetamide: $CH_3$—CO—$NH_2$) and the production of ammonia by both enzymes, a better understanding of the function of the *H. pylori* UreI protein is required. This understanding will open new opportunities for the prevention and treatment of *H. pylori* infections.

SUMMARY OF THE INVENTION

This invention provides methods for identifying molecules capable of inhibiting the growth and/or survival of Helicobacter species, particularly, *H. pylori*, in vivo. In particular, the methods of this invention involve screening molecules that specifically inhibit UreI protein function.

The invention encompasses the molecules identified by the methods of this invention and to the use of the molecules by the methods of this invention to treat or prevent Helicobacter, and particularly *H. pylori*, infection in humans and animals.

Another aspect of this invention is a method of preventing or treating Helicobacter species infection by administration to a human or animal in need of such treatment a molecule capable of inhibiting the growth and/or survival of Helicobacter species in vivo. One such molecule according to this invention is characterized by a high affinity for UreI, which allows it either to be transported inside the Helicobacter cell or to inhibit export properties of UreI. By inhibiting UreI, such molecule renders the bacteria more sensitive to acidity.

Yet another aspect of this invention is the production of immunogenic UreI antigens and their use as vaccines to prevent Helicobacter species infection and/or colonization of the gut. Antibodies to these UreI antigens are also encompassed within the scope of this invention.

This invention further relates to recombinant strains of *H. pylori* comprising a modified ureI gene, such that the products of the modified gene contribute to the attenuation of the bacteria's ability to survive in vivo, and thus, its pathogenic effects.

BRIEF DESCRIPTION OF THE FIGURES

FIG. 1 depicts the urease gene cluster of *H. pylori* parental strains N6 and SS1 and of the derived mutants deficient in UreI, strains N6-823, N6-834, and SS1-834. The genes are indicated by boxes with an arrow showing the direction of their transcription. The distances between the ure genes are given in base pairs, bp. The site hybridizing to the primers used to confirm correct allelic exchange in strains N6-823, N6-834, and SS1-834 is shown. Blank boxes represent the cassettes containing the genes conferring, resistance to Cm (cat) or to Km (aphA-3). The urease activity of these strains is given on the right-hand side of the figure. Urease activity was measured as the release of ammonia on crude extracts of bacteria grown 48 hours on blood agar plates as described previously (7). One unit corresponds to the amount of enzyme required to hydrolyze 1 $\mu$mol of urea $min^{-1}$ $mg^{-1}$ total protein. The data are means±standard deviation calculated from 3 to 5 determinations.

FIG. 2 depicts a restriction map of pILL823, pILL824, pILL833, pILL834, and pILL845. Small boxes mark the vector of each plasmid, large boxes correspond to genes. Ori indicates the position of the ColE1 origin of replication, repA the gene coding for the RepA protein necessary for autonomous replication of pHel2 in *H pylori*. $Sp^R$, $Ap^R$, and $Cm^R$ are the genes conferring resistance to spectinomycin, ampicillin, and chloramphenicol, respectively. The sequence of the DNA region comprising the ureI stop codon and the ureE start codon, including the BclI site where adaptor H19 was inserted, is given. Plasmid pILL825 was produced by insertion of H 19 into the BclI site of plasmid pILL824; the resulting ureI-ureE intergenic sequence is also shown. The stop codon of ureI and the start codon of ureE are boxed and the ribosome binding site (RBS) is underlined. Brackets indicate the position of restriction sites removed by ligation.

FIG. 3 shows the alignment of the amino acid sequence of UreI from *H. pylori* with those of similar proteins and prediction of the two-dimensional structure of members of the UreI/AmiS protein family. Residues identical at one position in, at least, four sequences are boxed, dashes indicate gaps inserted to optimize alignment. The organisms from which the sequences originated and the degree of identity with the *H. pylori* UreI protein are: UreI-Hp, *Helicobacter pylori* (195 residues, accession No. M84338 (SEQ ID NO:10)); UreI-Hf, *Helicobacter felis* (74% identity over 196 residues, accession No. A41012 (SEQ ID NO:11)); UreI-Lacto, *Lactobacillus fermentum* (55% identity over the 46 residues-long partial sequence, accession No. D10605 (SEQ ID NO: 12)); UreI-Strepto, *Streptococcus salivarius* (54% identity over the 129 residues-long partial sequence, accession No. U35248 (SEQ ID NO:13)); AmiS-Myco, *Mycobacterium smegmatis* (39% identity over 172 residues, accession No. X57175 (SEQ ID NO:14)); AmiS-Rhod, Rhodococcus sp. R312 (37% identity over 172 residues accession No. Z46523 (SEQ ID NO:15)) and AmiS-Pseudo, *Pseudomonas aeruginosa* (37% identity over 171 residues, accession No. X77161 (SEQ ID NO:16)). Predicted transmembrane α-helices are shown as shaded boxes. The regions separating these boxes are hydrophilic loops labeled "IN" when predicted to be intracellular and "OUT" when predicted to be extracellular.

DETAILED DESCRIPTION

The urease cluster of Helicobacter species is unique among the many urease operons of Gram-negative bacteria that have been sequenced (20) in that it has an extra gene, ureI. The function of UreI has therefore been the subject of much speculation. It has mostly been attributed the function of an accessory protein required for nickel incorporation at the urease active site or a nickel transporter. It is now demonstrated that UreI is not required for full activation of *H. pylori* urease during in vitro growth. UreI is, thus, not a nickel transporter since such a protein, NixA (3) already identified in *H. pylori,* is necessary for full urease activity. It is also demonstrated herein that replacing ureI with a non-polar cassette has no effect on urease activity as measured in vitro. This is the first time that a non-polar cassette (19) has been shown to be functional in *H. pylori*. These results provide a valuable tool for genetic analysis of complex *H. pylori* operons, such as Cag, a multigenic pathogenicity island.

It is demonstrated herein that UreI is essential for Helicobacter survival its vivo and/or colonization of mice. This may be due to reduced resistance to acidity of the ureI mutant as suggested by the results of survival in acidic conditions with 10 mM urea, described in the Examples that follow. UreI has a sequence similar to those of the AmiS proteins, proposed to be involved in the transport of short-chain amides (27), molecules structurally similar to urea. The UreI/AmiS proteins have the characteristics of integral membrane proteins, probably of the cytoplasmic membrane.

Different roles for UreI can tentatively be proposed. First, UreI might be involved in transport of urea or short-chain amides. This transport might be import or export or urea or short-chain amides. Alternatively, UreI might be involved in an uptake system for maintaining appropriate intracellular ammonia concentrations or UreI might be involved in export of intracellular ammonia. Finally, UreI might be involved in a mechanism of coupling ureaseactivity to the periplasmic pH, allowing urease to become more active at acidic pH.

The results of acidity survival experiments performed as described in the Examples that follow are best compatible with UreI being involved in ammonia export. An essential role for UreI as an amide transporter is less likely because a SS1 mutant, deficient in aliphatic amidase, colonize mice as efficiently as the parental strain in mouse colonization experiments. In addition, amidase activity is not significantly modified by the deletion of ureI in mutant strain N6-834. Whatever the role of UreI, as a membrane protein essential for the survival of *H. pylori* in vivo, it now provides a powerful target for new therapeutics and vaccines against *H. pylori*.

Molecules capable of inhibiting the growth and/or survival of Helicobacter in vivo may be identified by contacting a parental Helicobacter with said molecule in a biological sample; testing and comparing the acidity sensitivity of the parental strain to a strain deficient in UreI; selecting said molecules displaying a differential effect on the parental strain as compared to the UreI deficient strain; and collecting said active molecule. Acidity sensitivity can be tested by in vitro acidity resistance tests as described by Clyne et al. (8), incorporated herein by reference. These methods may be used to identify molecules that inhibit any Helicobacter species, including *Helicobacter pylori, helicobacter felis, Helicobacter helmannii, Helicobacter mustalae, Helicobacter canis, Helicobacter bilis,* and *Helicobacter hepaticus.*

The molecules identified by the methods of this invention are capable of inhibiting transport of urea or amide analogs. Preferably, these molecules are active even at low concentration. Suitable candidate molecules are structural analogs of urea and urease inhibitors, such as, for example, AHA (acetohydroxyamic acid), hydroxyurea, thiourea, hippuric acid, flurofamide, hydroxylamine, or methyl urea (29). Export of urea is consistent with the existence of a urea cycle, which is one of the characteristics of *H. pylori* (28). Thus, the molecules obtained according to the invention are urease specific inhibitors, are not competitive inhibitors, are not toxic or mutagenic in vivo, and potentialize the action of antibiotics or a bactericidal molecules.

One example of a molecule according to this invention is a monoclonal or polyclonal antibody specific for UreI. Preferably, the antibody is capable of specifically inhibitin the export of ammonia or urea by UreI.

The molecules of this invention may be administered in combination with a pharmaceutically acceptable carrier to a patient suffering from a Helicobacter infection. Alternatively, immunogenic compositions comprising one or more molecules according to this invention may be administered in a vaccine composition to prevent infection by Helicobacter species.

Immunogenic compositions according to this invention may also comprise all or part of the UreI protein. Preferably, the UreI fragments comprise at least 10 consecutive amino acids of the native UreI sequence and more preferably, the fragments comprise at least 18, 20, or 25 consecutive amino acids of the native UreI sequence. Other suitable UreI fragments may contain at least 40 or at least 100 consecutive amino acids of the native UreI sequence. Suitable fragments of *Helicobacter pylori* include, for example, fragments selected from the group consisting of amino acid residues 154 to 174, 94 to 105, 122 to 140, and 158 to 170 of *H. pylori* (GenBank accession No. M84338)

Reference will now be made to the following Examples. The Examples are purely exemplary of the invention and are not to be construed as limiting of the invention.

EXAMPLES

Construction of Defined Mutations of the *H. pylori* UreI Gene

*H. pylori* strains with defined mutations in ureI were generated by allelic exchange to determine whether the UreI protein was necessary for full urease activity. For this purpose, two plasmids (pILL823 and pILL834) with cassettes carrying antibiotic resistance genes inserted in ureI were constructed in *E. coli*.

In one plasmid, pILL823 (FIG. 2), the ureI gene was inactivated by insertion of a promoterless cat gene, conferring resistance to chloramphenicol (Cm). A 780 bp blunt-ended BamHI restriction fragment containing the "cat cartridge" from pCM4 (Pharmacia, Sweden) was introduced into a unique HpaI site, between codons 21 and 22 of ureI, in pILL753 (9). In the resulting plasmid, pILL823 (FIG. 2), cat is in the same orientation as ureI and is expressed under the control of the ureI promoter.

Figure 2:
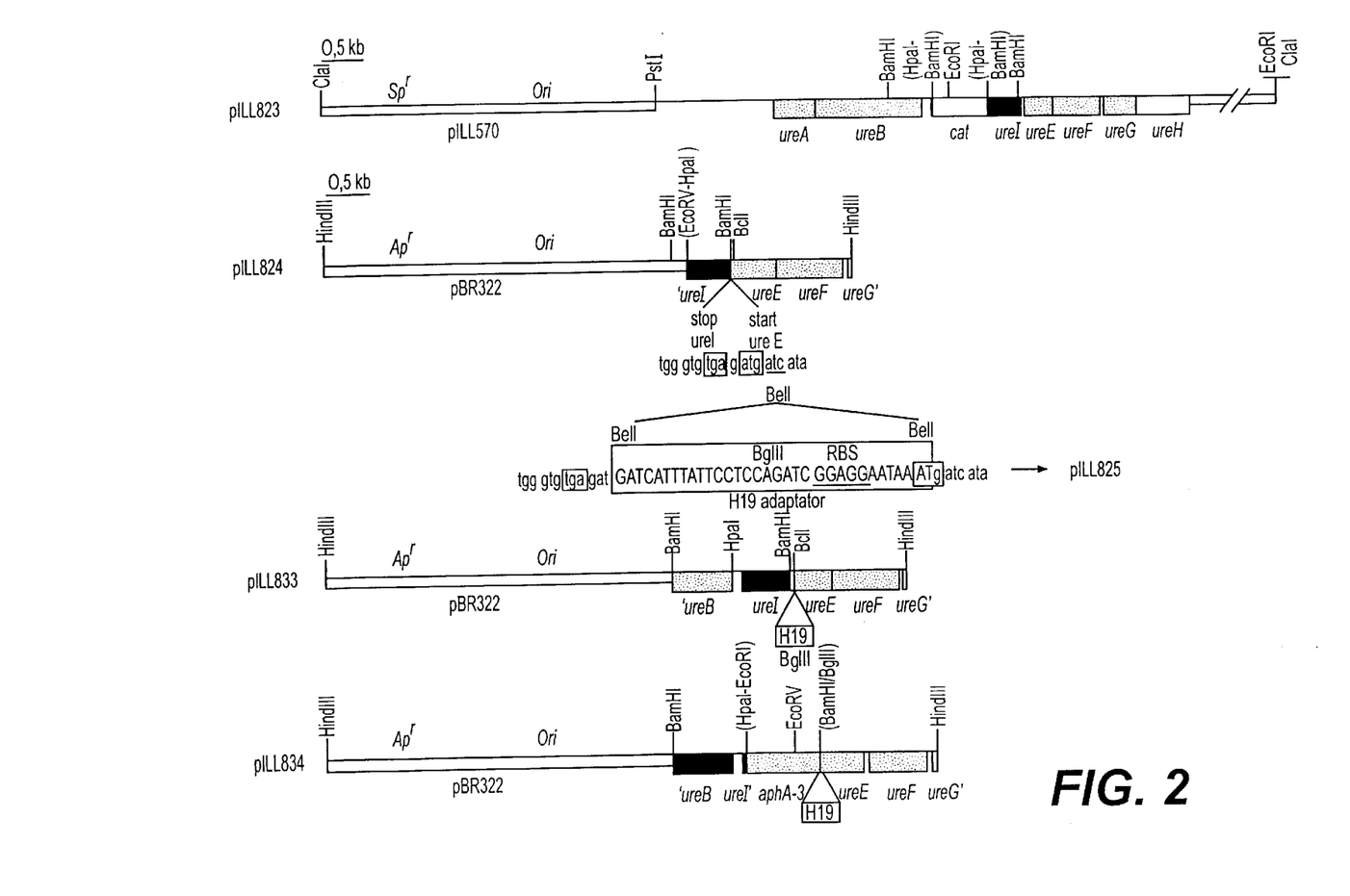

The second plasmid, pILL834, carried a ureI gene in which all but the first 21 codons were deleted and replaced with a non-polar cassette composed of the aphA-3 kanamycin (Km) resistance gene (25), which has been isolated from its own promoter and terminator regions (19). In *Shigella flexneri* (19) and other organisms (such as *Yersinia enterocolitica*, 2) this cassette has been shown not to affect the transcription of the genes downstream within an operon as long as these distal genes have intact translation signals. There is only one base pair separating ureI from ureE (FIG. 1) and ureE does not have an RBS (ribosome binding site) of its own, so the expression of ureI and ureE is transcriptionally and translationally coupled. Therefore, a ureI deletion was accompanied by the addition of an RBS immediately upstream from ureE. Three intermediates, pILL824, pILL825 and pILL833 (FIG. 2), were constructed in order to produce the final plasmid, pILL834 (FIG. 2). A 1.8 Kb HpaI-HindIII restriction fragment from pILL753 (9) was inserted between the ECoRV and HindIII sites of pBR322, to give pILL824. Insertion of the H19 adaptor (carrying an RBS and ATG in frame with ureE, Table 1) into a BclI site overlapping the two first codons of ureE in pILL824 produced pILL825 (FIG. 2). The BamHI fragment of pILL825 was then replaced by a 1.3 Kb blunt-ended PvuII-BamHI fragment from pILL753. This resulted in the reconstitution of a complete ureI gene, and this plasmid was called pILL833. Finally, pILL834 was obtained by replacement of the HpaI-BglII fragment of pILL833 (thereby deleting all but the first 21 codons of ureI) with an 850 bp blunt-ended EcoRI-BamHI fragment of pUC18K2 containing the non-polar Km cassette (19).

TABLE 1

Name and nucleotide sequence of oligonucleotides

| Primer | Oligodeoxynucleotide sequence (5' to 3') |
|---|---|
| H17 | TTTGACTTACTGGGGATCAAGCCTG (SEQ ID NO:1) |
| 19* | GATCATTTATTCCTCCAGATCTGGAGGAATAAAT (SEQ ID NO:2) |
| H28 | GAAGATCTCTAGGACTTGTATTGTTATAT (SEQ ID NO:3) |
| H34 | TATCMCGGTGGTATATCCAGTG (SEQ ID NO:4) |
| H35 | GCAGTTATTGGTGCCCTTAAACG (SEQ ID NO:5) |
| H50 | CCGGTGATATTCTCATTTTAGCC (SEQ ID NO:6) |
| 8A | GCGAGTATGTAGGTTCAGTA (SEQ ID NO:7) |
| 9B | GTGATACTTGAGCAATATCTTCAGC (SEQ ID NO:8) |
| 12B | CAAATCCACATAATCCACGCTGAAATC (SEQ ID NO:9) |

*H19 was used as adaptor and the others were used as primers for PCR amplification.

Introduction of UreI Mutations into *H. pylori*

*H. pylori* ureI mutants were produced by allelic exchange following electroporation with a concentrated preparation of pILL823 and pILL834 as previously described by Skouloubris et al. (23) from *H. pylori* strain N6 (12) and from the mouse-adapted *H. pylori* strain, SS1 (Sydney Strain, 17). Bacteria with chromosomal allelic exchange with pILLS23 were selected on Cm (4 μg/ml) and those with chromosomal allelic exchange with pILL834 on Km (20 μg/ml). It was determined that the desired allelic exchange had taken place in strains N6-823, N6-834, and SS1-834 (FIG. 1) by performing PCR with the appropriate oligonucleotides (Table 1). The PCR products obtained with genomic DNA of these strains were as expected (i) for strain N6-823: 140 bp with primers H28-H34, 220 bp with H35-9B, and 1.2 Kb with H28-9B, and (ii) for strains N6-834 and SS1-834, 150 bp with primers H28-H50, 180 bp with H17-12B, and 1 Kb with H28-12B.

The growth rate of strain N6-834 carrying a non-polar deletion of ureI was compared to that of the parental strain N6. No difference in the colony size was observed on blood agar medium plates. Identical doubling times and stationary phase OD were measured for both strains grown in BHI (Oxoid) liquid medium containing 0.2% β-cyclodextrin (Sigma). Thus, UreI is not essential for *H. pylori* growth in vitro.

Urease activity of *H. pylori* UreI Mutants

The urease activity of strains N6-823, N6-834, and SS1-834 was measured in vitro as described previously by Cussac et al. (9) and compared to the activity of the parental strains, N6 and SS1 (FIG. 1). Urease activity was almost completely abolished in strain N6-823 (0.3±0.1 units). Strains N6-834 and SS1-834, with non-polar ureI mutations had wild-type levels of activity (N6-834 and SS1-834: 12±2 units; parental strains, N6: 10±1 and SS1: 12±0.4 units).

These results strongly suggest that the urease-negative phenotype of the N6-ureI::TnKm-8 (13) and the very weak urease activity of N6-823 strains were due to a polar effect of the inserted cassettes on the expression of the downstream genes ureE and ureF (FIG. 1). This hypothesis was tested by measuring urease activity of strain N6-823 complemented in trans with an *E. coli*/*H. pylori* shuttle plasmid expressing the ureE–F genes. This plasmid, pILL845 (FIG. 2), was obtained by insertion of a 2.8 Kb ClaI-BamHI fragment of pILL834 (comprising the 3'-end of ureB, the non-polar deletion of ureI and intact ureE and ureF genes) into the corresponding sites of the shuttle vector pHe12 constructed by Heuermann and Haas (15). Strain N6-823 was electroporated with a DNA preparation of pILL845 as described by Skouloubris et al. (23), and transformants were selected on kanamycin (20 μg/ml) and chloramphenicol (4 μg/ml). In strain N6-823 harboring pILL845, wild type urease activity was recovered confirming that the very low urease activity of strain N6-823 was due to a polar effect on the expression of the accessory genes ureE–F. In *Klebsiella aerogenes*, the absence of UreE has little effect on urease activity (4). In contrast, UreF, part of the accessory protein complex (UreDFG), is absolutely required for the production of active urease (21). Thus, by analogy, it is likely that the phenotype of the *H. pylori* polar ureI mutants was due to the absence of ureF expression.

Colonization Test for the *H. pylori* SS1-834 Mutant in the Mouse Animal Model

The mouse model for infection by the *H. pylori* SS1 strain (Sydney Strain, 17), validated by Chevalier et al. (7) and Ferrero et al. (14), was used to test the function of UreI in vivo. Mice were infected with the non-polar treI mutant, SS1-834, and with the parental strain, SS1, (which had gone through an equivalent number of in vitro subcultures) as a positive control. This experiment was repeated three times and produced identical results. Two independently constructed SS1-834 mutants were used. The first mutant strain had gone through 30 in vitro subcultures, the second only 20. Under the same experimental conditions, strain SS1 can undergo more than 80 in vitro subcultures without loosing its colonization capacity.

In each experiment, aliquots (100 µl) containing $10^6$ H. pylori strain SS1 or SS1-834 bacteria prepared in peptone broth were administered orogastrically to 10 mice each (six to eight-weeks old Swiss specific-pathogen-free mice) as described by Ferrero et al. (14). Mice were killed four weeks after inoculation. The presence of H. pylori was tested wvith a direct urease test on biopsies performed on half the stomach (14). The remaining gastric tissues were used for quantitative culture of H. pylori as described by Ferrero et al. (14). In each experiment, the stomachs of the ten SS1-infected mice all tested positive for urease. The bacterial load was between $5\times10^4$ and $5\times10^5$ colony forming units (CFU) per g of stomach. None of the stomachs of the mice infected with strain SS1-834 tested positive for urease and no H. pylori cells were cultured from them. Thus, the UreI protein is essential for the H. pylori in vivo survival and/or colonization of the mouse stomach.

Survival of the H. pylori N6-834 Mutant in Acidic Conditions

Survival to acidic conditions in the presence or absence of 10 mM urea was tested with strains N6 and N6-834. The experimental procedures were those described in Clyne et al. (8). Exponentially grown bacteria were harvested, washed in PBS (phosphate buffer saline), and approximately $2\times10^8$ CFU/ml were resuspended in PBS of pH 2.2 or pH 7 in the presence or absence of 10 mM urea and incubated for one hour at 37° C. To evaluate bacterial survival, quantitative cultures of the H. pylori strains were performed.

In agreement with the results reported by Clyne et al. (8), at pH 7, none of the strains survived in the presence of urea because of a final pH rise above 8. At pH 7 in the absence of urea, both strains survived similarly ($10^8$ CFU/ml). As expected based on the results of Clyne et al. (8), both strains were killed at pH 2.2 in the absence of urea and significant survival at pH 2.2 in the presence of urea was observed with strain N6 ($5\times10^6$ CFU/ml, final pH=6.5).

In contrast, when the non-polar ureI mutant strain N6-834 was incubated at pH 2.2 in the presence of urea, very low survival was observed ($10^2$ CFU/ml) and the pH was unchanged (pH 2.2) after one hour incubation.

Alignment of the UreI and AmiS Protein Sequences and Two Dimensional Structure Prediction A systematic search for UreI homologs in the protein data banks was carried out. It was determined that H. pylori is not the only ureolytic bacterium with a ureI gene. Two phylogenetically related Gram-positive organisms, *Streptococcus salivarius*, a dental plaque bacterium (6), and *Lactobacillus fermentum*, a lactic acid bacterium (16), carry genes (the available sequences are only partial) coding for UreI-homologs (FIG. 3) located immediately upstream from the urease structural genes. The ureI gene has been detected in various Helicobacter species; the H. felis urea gene has been entirely sequenced (FIG. 3 and allowed U.S. patent application Ser. No. 08/467,822, the entire contents of which are incorporated herein by reference). PCR experiments have suggested that there is a ureI gene in H. heilmannii (24) and in H. mustelae.

Sequence similarities between the UreI protein of H. pylori and the AmiS proteins expressed by the aliphatic amidase operons from *P. aeruginosa* (27) and Rhodococcus sp. R312 (5) have been reported. In *Mycobacterium smegmatis*, there is an additional AmiS-homolog encoded by a gene, ORF P3, located immediately upstream from an amidase gene (18).

Figure 3:
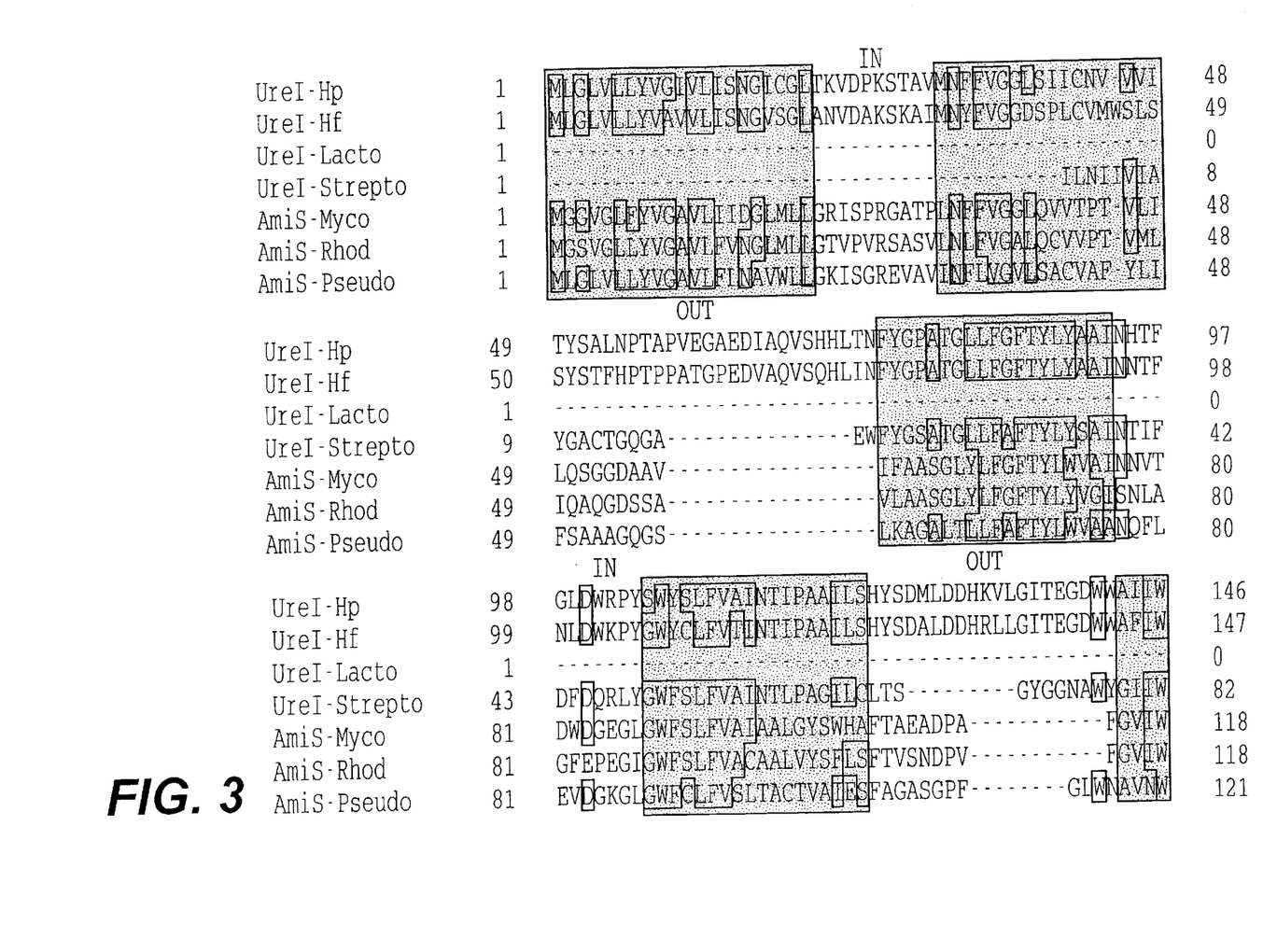

Alignment of these UreI/AmiS proteins [using the Clustal W(1. 60) program] defined strongly conserved stretches of amino acids (FIG. 3). All but one of these conserved blocks are in highly hydrophobic segments. These regions, each 17 to 22 residues long, are probably folded into transmembrane α-helices (FIG. 3). Six transmembrane regions were predicted for the proteins from H. pylori, H. felis, and P. aeruginosa and seven for those from Rhodococcus sp. R312 and M. smegmatis (highly reliable predictions, performed with pHD, a profile fed neural network system as described by Rost et al. (22)). The orientation of the UreI/AmiS proteins in the membrane was deduced from the charges of the intercalated hydrophilic regions, which are short in these proteins (FIG. 3). The first five such regions are poorly conserved and of various length. The last interhelical segment common to these proteins is significantly more conserved than the others. This region predicted to be intracellular may be the active site of UreI or a site of multimerization or interaction with an intracellular partner. These results strongly suggest that the members of the UreI/AmiS family, found in both Gram-positive and -negative bacteria, are integral membrane proteins. These proteins have no signal sequence and should therefore be inserted into the cytoplasmic membrane in Gram-negative bacteria.

The references cited herein are specifically incorporated by reference in their entirety.

REFERENCES

1. Akada, J. K., M. Shirai, H. Takeuchi, M. Tsuda, and T. Nakazawa. 1997. Transcriptional analysis of urease structural gene and the ureI gene in *Helicobacter pylori* Gut. 41:A9.
2. Allaoui, A., Schulte, R. and G. R. Cornelis. 1995. Mutational analysis of the *Yersinia enterocolitica* virC operon: characterization of yscE, F, G, H, I, J, K required for Yop secretion andysch encoding YopR. Mol. Microbiol. 18:343–355.
3. Bauerfeind, P., R. M. Garner, and H. L. T. Mobley. 1996. Allelic exchange mutagenesis of nixA in *Helicobacter pylori* results in reduced nickel transport and urease activity. Infect. Immun. 64:2877–2880.
4. Brayman, T. G., and R. T. Hausinger. 1996. Purification, characterization, and functional analysis of a truncated *Klebsiella aerogenes* UreE urease accessory protein lacking the Histidine-Rich carboxyl terminus. J. Bacteriol. 178:5410–5416.
5. Chebrou, H., F. Bigey, A. Arnaud, and P. Galzy. 1996. Amide metabolism: a putative ABC transporter in Rhodococcus sp. R312. Gene. 182:215–218.
6. Chen, Y.-Y. M., K. A. Clancy, and R. A. Burne. 1996. *Streptococcus salivarius* urease: genetic and biochemical characterization and expression in a dental plaque Streptococcus. Infect. Immun. 64:585–592.
7. Chevalier, C., J.-M. Thiberge, R. L. Ferrero, and A. Labigne. 1998. Essential role of *Helicobacter pylori* g-Glutamyltranspeptidase (GGT) for the colonization of the gastric mucosa in mice. Mol. Microbiol. Submitted.
8. Clyne, M., A. Labigne, and B. Drumm. 1995. *Helicobacter pylori* requires an acidic environment to survive in the presence of urea. Infect. Immun. 63:1669–1673.
9. Cussac, V., R. L. Ferrero, and A. Labigne. 1992. Expression of *Helicobacter pylori* urease genes in *Escherichia* coli grown under nitrogen-limiting conditions. J. Bacteriol. 174:2466–2473.
10. Dunn, B. E., H. Cohen, and M. Blaser. 1997. *Helicobacter pylori*. Clin. Microbiol. Rev. 10:720–741.
11. Eaton, K. A., and S. Krakowka. 1994. Effect of gastric pH on urease-dependent colonization of gnotobiotic piglets by *Helicobacter pylori*. Infect. Immun. 62:3604–3607.
12. Ferrero, R. L., V. Cussac, P. Courcoux, and A. Labigne. 1992. Construction of isogenic urease-negative mutants of *Helicobacter pylori* by allelic exchange. J. Bacteriol. 174:4212–4217.
13. Ferrero, R. L., V. Cussac, P. Courcoux, and A. Labigne. 1994. Construction of isogenic mutants of *Helicobacter pylori* deficient in urease activity. pp179–182. In Basic and Clinical Aspects of *H. pylori* infection. Springer-Verlag Berlin Heidelberg.
14. Ferrero, R. L., J.-M. Thiberge, M. Huerre, and A. Labigne. 1998. Immune responses of specific-pathogen-free mice to chronic *Helicobacter pylori* (strain SS1) infection. Infect. Immun. 66 in press.
15. Heuermann, D., and R. Haas. 1998. A stable shuttle vector system for efficient genetic complementation of *Helicobacter pylori* strains by complementation and conjugation. Mol. Gen. Genet. 257:519–528.
16. Kakimoto, S., Y. Sumino, K. Kawahara, E. Yamazaki, and I. Nakatsui. 1990. Purification and characterization of acid urease from *Lactobacillus fermentum*. Appl. Microbiol. & Biotechnol. 32:538–543.
17. Lee, A., J. O'Rourke, M. Corazon De Ungria, B. Robertson, G. Daskalopoulos, and M. F. Dixon. 1997. A standardized mouse model of *Helicobacter pylori* infection: introducing the Sydney Strain. Gastroenterology. 112:1386–1397.
18. Mahenthiralingam, E., P. Draper, E. O. Davis, and M. J. Colston. 1993. Cloning and sequencing of the gene which encodes the highly inducible acetamidase of *Mycobacteriun smegmatis*. J. Gen. Microbiol. 139:575–583.
19. Menard, R., P. J. Sansonetti, and C. Parsot. 1993. Nonpolar mutagenesis of the ipa genes defines IpaD, IpaC, and IpaD as effectors of *Shigella flexneri* entry into epithelial cells. J. Bacteriol. 175:5899–5906.
20. Mobley, H. L. T., M. D. Island, and R. P. Hausinger. 1995. Molecular biology of ureases. Microbiol. Rev. 59:451–480.
21. Moncrief, M. B. C., and R. P. Hausinger. 1997. Characterization of UreG, identification of a UreD-UreF-UreG complex, and evidence suggesting that a nucleotide-binding site in UreG is required for in vivo metallocenter assembly of *Klebsiella aerogenes* urease. J. Bacteriol. 179:4081–4086.
22. Rost, B., R. Casadio, P. Fariselli, and C. Sander. 1995. Prediction of helical transmembrane segments at 95% accuracy. Prot. Science. 4:521–533.
23. Skouloubris, S., A. Labigne, and H. De Reuse. 1997. Identification and characterization of an aliphatic amidase in *Helicobacter pylori*. Mol. Microbiol. 25:989–998.
24. Solnick, J. V., J. O'Rourke, A. Lee, and L. S. Tompkins. 1994. Molecular analysis of urease genes from a newly identified uncultured species of Helicobacter. Infect. Immun. 62:1631–1638.
25. Trieu-Cuot, P., G. Gerbaud, T. Lambert, and P. Courvalin. 1985. In vivo transfer of genetic information between Gram-positive and Gram-negative bacteria. EMBO J. 4:3583–3587.
26. Williams, C. L., T. Preston, M. Hossack, C. Slater, and K. E. L. McColl. 1996. *Helicobacter pylori* utilizes urea for amino acid synthesis. FEMS Immunol. Med. Microbiol. 13:87–94.
27. Wilson, S. A., R. J. Williams, L. H. Pearl, and R. E. Drew. 1995. Identification of two new genes in the *Pseudomonas aeruginosa* amidase operon, encoding an ATPase (AmiB) and a putative integral membrane protein (AmiS). J. Biol. Chem. 270:18818–18824.
28. Mendz, G. L. and S. L. Mazell. 1996. The Urea Cycle of *Helicobacter pylori*. Microbiology 142:2959–2967.
29. Nicholson, E. V., E. A. Concaugh and H. L. T. Mobley. 1991. Infection and Immunity. 59(10):3360–3365.

We claim:

1. A method of selecting a test molecule comprising:
preparing a wild-type biological sample at a first pH, wherein the biological sample contains wild-type Helicobacter;
preparing a UreI-deficient biological sample at the first pH, wherein the biological sample contains UreI-deficient Helicobacter;
adding a test molecule at the same concentration to each of the wild-type and UreI-deficient biological samples;
reducing the pH of the wild-type and the pH of the UreI-deficient biological samples to a second pH;
comparing the growth or survival of the wild-type and UreI-deficient biological samples in the first pH and the second pH; and
selecting a test molecule that reduces the growth or survival of the wild-type Helicobacter to a greater extent than the survival of the UreI-deficient Helicobacter.

2. A method comprising:
preparing a wild-type biological sample at a pH less than 7, wherein the biological sample contains wild-type Helicobacter;
preparing a UreI-deficient biological sample at the same pH, wherein the biological sample contains UreI-deficient Helicobacter;
adding a test molecule at a first concentration to each of the wild-type and UreI-deficient biological samples;
increasing the concentration of the test molecule in the wild-type biological sample to a second concentration and increasing the concentration of the test molecule in the UreI-deficient biological samples to said second concentration;
comparing the growth or survival of the wild-type and UreI-deficient biological samples in the first concentration and the second concentration of the test molecule; and
selecting a test molecule that reduces the growth or survival of the wild-type Helicobacter to a greater extent than the survival of the UreI-deficient Helicobacter.

3. The method of selecting a test molecule of claim 1 or claim 2, wherein the wild-type Helicobacter are selected from *Helicobacter pylori, Helicobacter felis, Helicobacter helmanii, Helicobacter mustalae, Helicobacter canis, Helicobacter bills,* and *Helicobacter hepaticus.*

4. The method of selecting a test molecule of claim 1 or claim 2, wherein the UreI-deficient Helicobacter are selected from *Heicobacter pylori, Helicobacter felis, Helicobacter helmanii, Helicobacter mustalae, Helicobacter canis, Helicobacter bills,* and *Helicobacter hepaticus.*

5. The method of selecting a test molecule of claim 1 or claim 2, wherein the wild-type Helicobacter and the UreI-deficient Helicobacter are selected from *Helicobacter pylori, Helicobacter felis, Helicobacter helmanii, Helicobacter mustalae, Helicobacter canis, Helicobacter bills,* and *Helicobacter hepaticus.*

6. The method of selecting a test molecule of claim 1 or claim 2, wherein at least one of the wild-type Helicobacter and the UreI-deficient Helicobacter are *Helicobacter pylori.*

7. The method of selecting a test molecule of claim 6, wherein the wild-type Helicobacter and the UreI-deficient Helicobacter are *Helicobacter pylori.*

8. The method of selecting a test molecule of claim 1, or claim 2, wherein the UreI-deficient Helicobacter exhibits wild-type levels of urease activity.

9. The method of selecting a test molecule of claim 1 or claim 2, wherein the UreI-deficient Helicobacter was deposited at CNCM on Jun. 28, 1999 under the accession number I-2246.

* * * * *

UNITED STATES PATENT AND TRADEMARK OFFICE
CERTIFICATE OF CORRECTION

PATENT NO. : 6,416,968 B1
DATED : July 9, 2002
INVENTOR(S) : Hilde De Ruse et al.

It is certified that error appears in the above-identified patent and that said Letters Patent is hereby corrected as shown below:

Column 19,
Lines 54, 58, 62 and 65, "Urel-deficient" should read -- UreI-deficient --.
Lines 55-56, "Urel-deficient" should read -- UreI-deficient --.

Column 20,
Line 34, "Urel-deficient" should read -- UreI-deficient --.
Lines 40, 45 and 51, "*bills*" should read -- *bilis* --.
Line 59, after "claim 1" delete the comma.

Signed and Sealed this

Fifth Day of November, 2002

*Attest:*

*Attesting Officer*

JAMES E. ROGAN
*Director of the United States Patent and Trademark Office*